(12) United States Patent
Kazakevich

(10) Patent No.: US 7,733,584 B2
(45) Date of Patent: Jun. 8, 2010

(54) COLOR-CORRECTED OPTICAL SYSTEM

(75) Inventor: Yuri Kazakevich, Andover, MA (US)

(73) Assignee: Smith & Nephew, Inc., Memphis, TN (US)

( * ) Notice: Subject to any disclaimer, the term of this patent is extended or adjusted under 35 U.S.C. 154(b) by 469 days.

(21) Appl. No.: 11/744,810

(22) Filed: May 4, 2007

(65) Prior Publication Data

US 2008/0273247 A1 Nov. 6, 2008

(51) Int. Cl.
G02B 9/04 (2006.01)
A61B 1/00 (2006.01)

(52) U.S. Cl. .................. 359/793; 359/637; 600/101

(58) Field of Classification Search ......... 359/793–796, 359/637, 362
See application file for complete search history.

(56) References Cited

U.S. PATENT DOCUMENTS

| | | | |
|---|---|---|---|
| 4,993,817 A | 2/1991 | Hoogland | |
| 5,142,410 A | 8/1992 | Ono et al. | |
| 5,198,931 A | 3/1993 | Igarashi | |
| 5,359,453 A | 10/1994 | Ning | |
| 5,519,532 A | 5/1996 | Broome | 359/435 |
| 5,538,497 A | 7/1996 | Hori | 600/182 |
| 5,582,576 A | 12/1996 | Hori et al. | 600/167 |
| 5,603,687 A | 2/1997 | Hori et al. | 600/166 |
| 5,662,584 A | 9/1997 | Hori et al. | 600/103 |
| 5,876,327 A * | 3/1999 | Tsuyuki et al. | 600/112 |
| 5,895,350 A | 4/1999 | Hori | 600/167 |
| 5,936,773 A | 8/1999 | Togino | 359/630 |
| 5,954,634 A | 9/1999 | Igarashi | 600/109 |
| 6,025,873 A | 2/2000 | Nishioka et al. | 348/72 |
| 6,038,079 A * | 3/2000 | Michaels | 359/661 |
| 6,069,651 A * | 5/2000 | Tsuyuki et al. | 348/75 |
| RE37,356 E | 9/2001 | Hori et al. | 600/103 |
| 6,450,949 B1 | 9/2002 | Farkas et al. | 600/168 |
| 6,530,882 B1 | 3/2003 | Farkas et al. | 600/168 |
| 6,574,042 B2 | 6/2003 | Allio | 359/463 |
| 6,853,485 B2 | 2/2005 | Hoogland | 359/435 |

FOREIGN PATENT DOCUMENTS

| | | |
|---|---|---|
| JP | 10-137174 | 5/1998 |
| JP | 3651477 B | 3/2005 |
| WO | 99/19752 | 4/1999 |

OTHER PUBLICATIONS

International Search Report and Written Opinion of the International Searching Authority issued in PCT/US2008/061267 mailed Oct. 30, 2008 (16 pages).

* cited by examiner

*Primary Examiner*—Jordan M. Schwartz
(74) *Attorney, Agent, or Firm*—Fish & Richardson P.C.

(57) ABSTRACT

An optical device includes an elongated tube configured for insertion into a body and optical members located in the tube. The optical members are configured to have an optical invariant-to-clear aperture semidiameter ratio greater than about 0.05 and an optical path difference less than about a value of the optical invariant divided by at least 250 times a midrange wavelength in a spectral range from about 435.8 nm to about 656.3 nm, and are preferably formed of an extraordinary dispersion optical material. A method includes conducting polychromatic light through at least one optical member located in an elongated tube configured for insertion into a body, where the optical members have an optical invariant-to-clear aperture semidiameter ratio greater than about 0.05 and an optical path difference less than about a value of an optical invariant divided by at least 250 times the midrange wavelength from about 435.8 to about 656.3 nm.

18 Claims, 13 Drawing Sheets

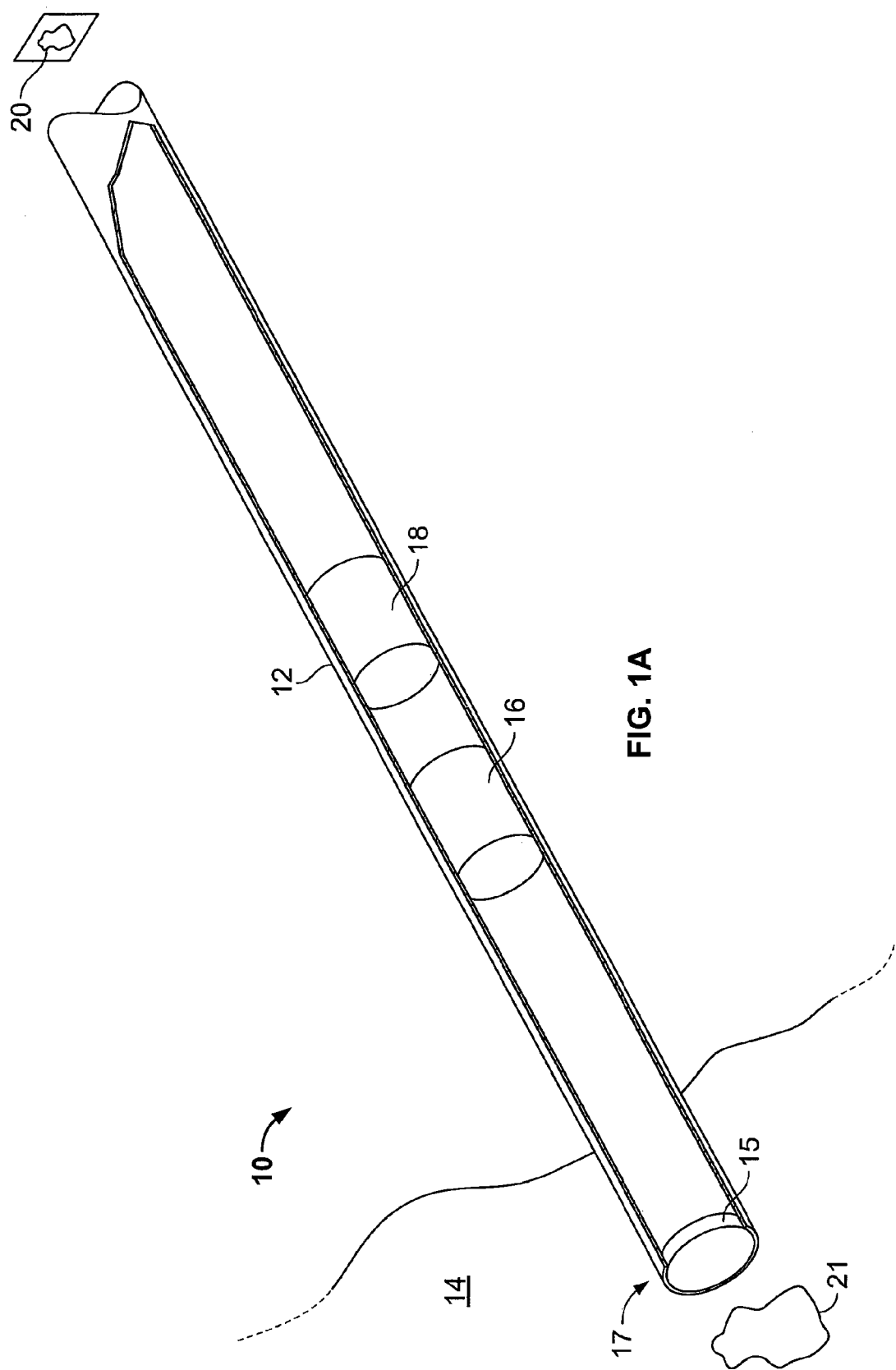

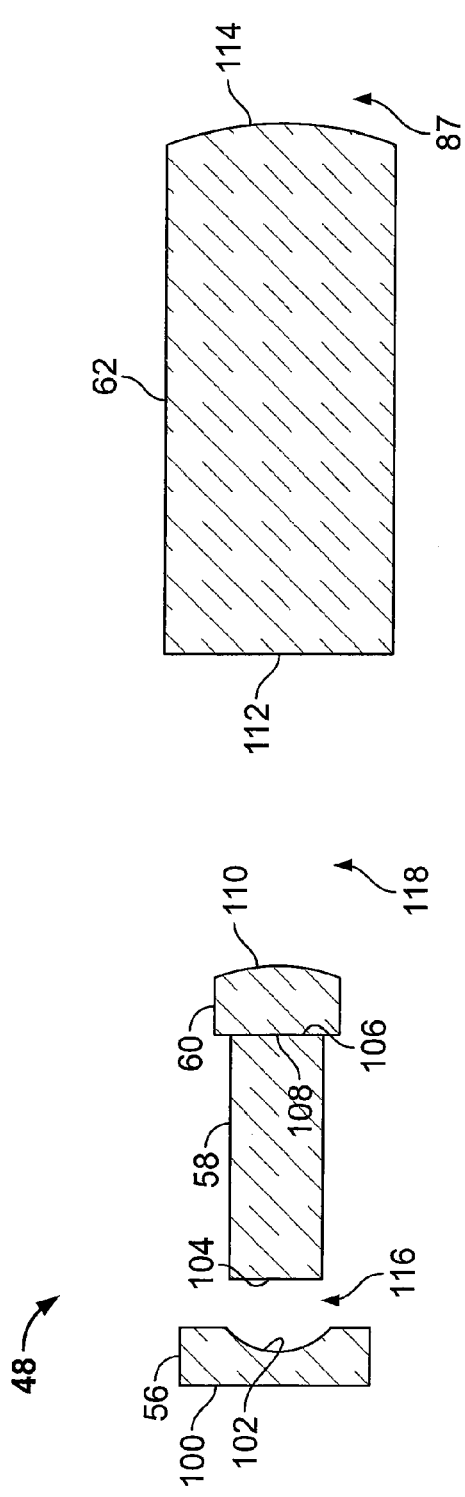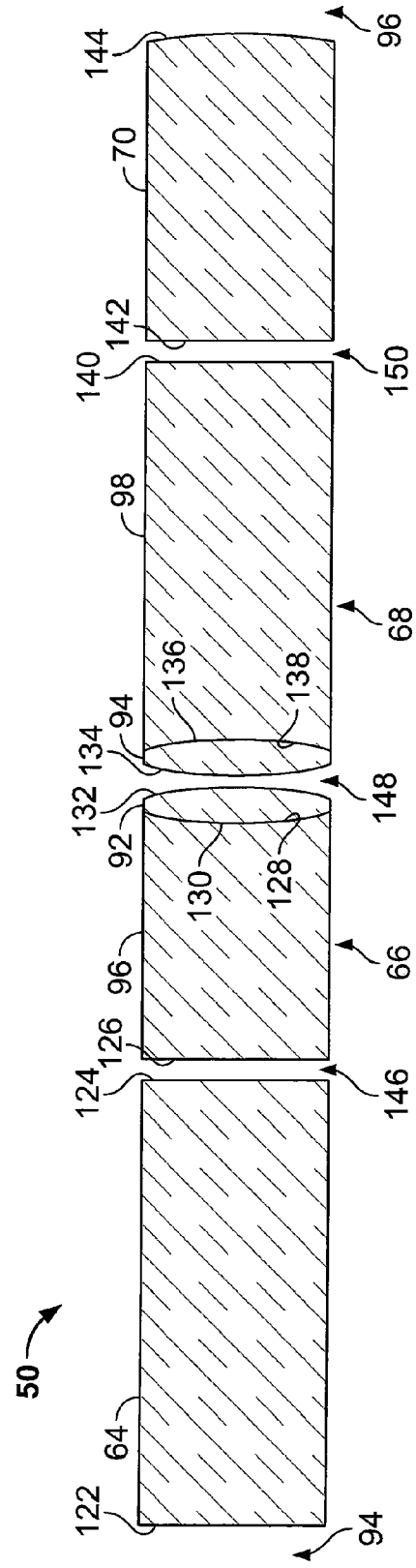

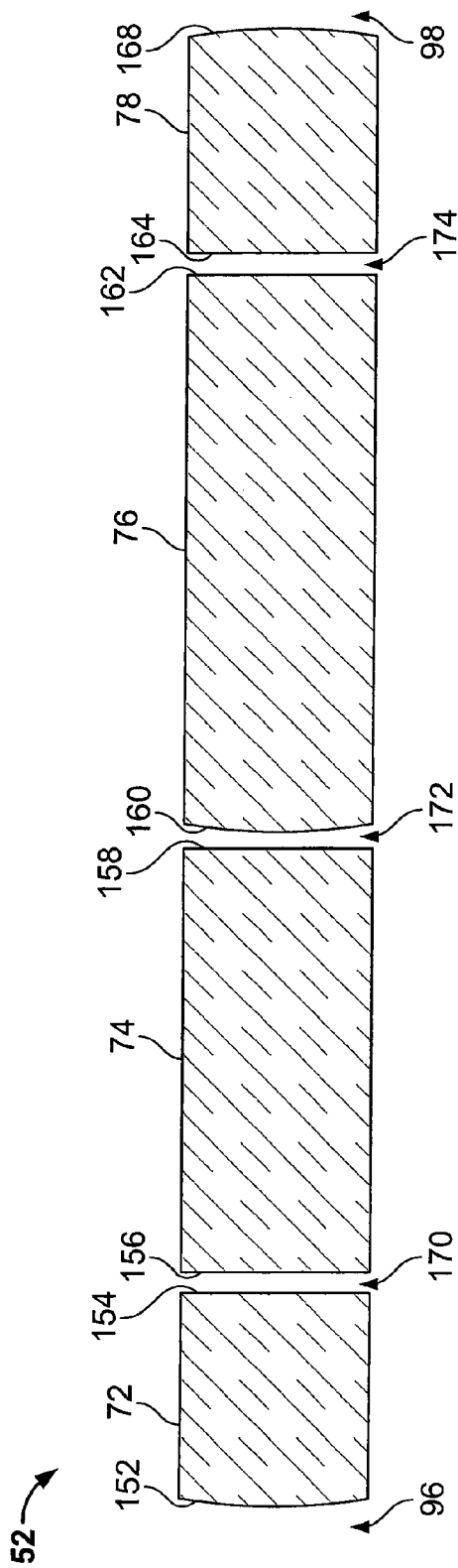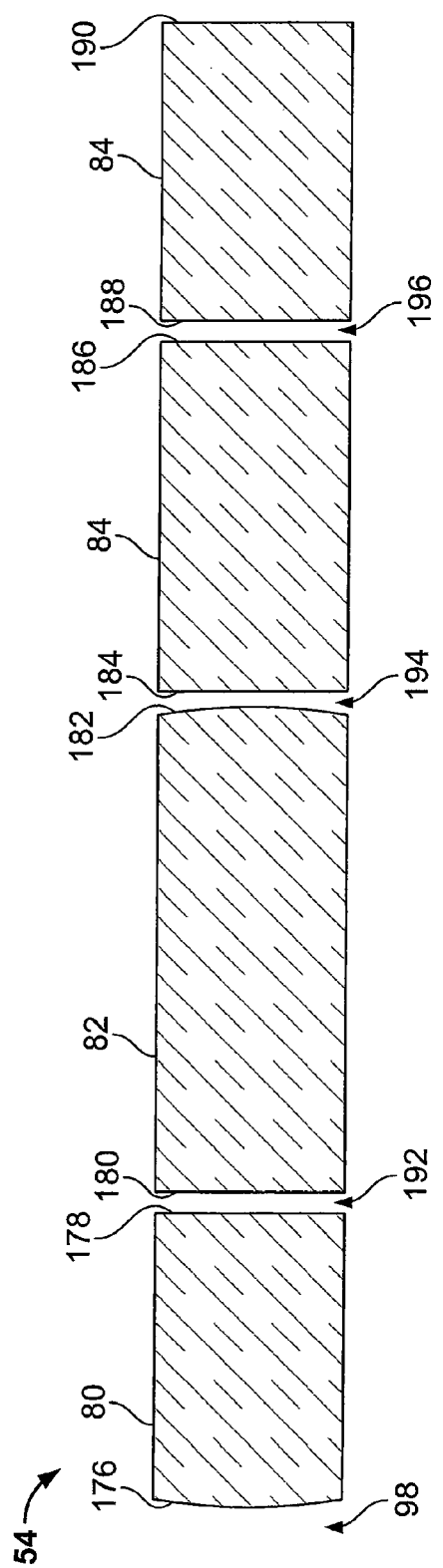
FIG. 11
FIG. 12

COLOR-CORRECTED OPTICAL SYSTEM

TECHNICAL FIELD

This description relates to an optical system that is corrected for chromatic aberrations.

BACKGROUND

Optical devices such as endoscopes are used to view the interior of a body, such as an internal cavity of a human body, for both diagnosis and treatment of medical conditions. Optical devices are also used to observe the interior of other bodies or objects that do not readily permit direct observation, for example, a borescope used to inspect nuclear fuel elements in nuclear reactors or rotors in turbomachinery, and similar optical devices are used to view the interior of scale-models of buildings in architectural endoscopy.

These optical devices, for example, an analog or digital camera or a video camera, are often coupled to an imaging device to visualize anatomy of the interior of the body. The images are useful in diagnosis, comparison, surgical or therapeutic procedures, medical review, training and the like. Lenses in the optical device relay an image of an object to the imaging device. Images produced by the imaging device are displayed on a monitor, for example, during surgical or therapeutic procedures. In color imaging systems, light rays of differing wavelengths incident on the lenses are refracted at different angles, resulting in chromatic aberrations.

Endoscopes designed for direct viewing and/or for viewing with video cameras are conventionally color-corrected to reduce chromatic aberrations in the spectral range from about 480 nanometers (nm) to about 644 nm.

SUMMARY

According to one general aspect, a color-corrected optical system that substantially corrects for chromatic aberrations in a spectral range from about 435.8 nm to about 656.3 nm includes an elongated tube configured for insertion into a body and at least two optical members are located in the tube. The optical members in combination are configured to have an optical invariant-to-clear aperture semidiameter ratio greater than about 0.05 and an optical path difference less than a value of an optical invariant divided by at least 250 times a midrange wavelength throughout the spectral range.

Implementations of this aspect may include one or more of the following features. For example, the optical members in combination are configured to have an optical path difference less than a value of an optical invariant divided by 320 times a midrange wavelength in the spectral range. The optical members in combination are configured to have an optical path difference less than a value of an optical invariant divided by 450 times a midrange wavelength in a spectral range. One or more of the optical members includes an extraordinary dispersion optical material. Another of the optical members includes a different extraordinary dispersion optical material.

One or more of the optical members includes an optical doublet. A pair of optical doublets are adjacent opposite sides of a pupil plane. Each optical doublet includes two lenses bonded to one another, and at least one of the lenses includes an extraordinary dispersion optical material. Each optical doublet includes a lens that includes an extraordinary dispersion optical material and another lens that includes a different extraordinary dispersion optical material. The extraordinary dispersion optical materials are N-KZFS11 and S-FPL53.

Each optical doublet includes a plano-concave rod lens bonded to a biconvex lens. Each optical doublet is axially aligned along an optical axis, the bi-convex lenses being adjacent opposite sides of a pupil plane. The device includes an objective group and at least one relay group, and the relay group nearest the objective group includes the optical doublet. An objective group and at least one relay group, and the relay group most distant from the objective group includes the optical doublet. There is a total of 18 lenses.

According to another general aspect, an optical member that includes an extraordinary dispersion optical material is located in an elongated tube configured for insertion into a body. An implementation of this aspect may include that the optical member is an optical doublet.

According to another general aspect, a method includes conducting light through one or more optical members located in an elongated tube configured for insertion into a body and substantially correcting for chromatic aberrations in a spectral range from about 435.8 nm to about 656.3 nm. The one or more optical members have an optical invariant-to-clear aperture semidiameter ratio greater than about 0.05 and an optical path difference less than a value of an optical invariant divided by at least 250 times a midrange wavelength in a spectral range from about 435.8 nm to about 656.3 nm.

Implementations of this aspect may include one or more of the following features. For example, the one or more optical members have an optical path difference less than a value of an optical invariant divided by 320 times a midrange wavelength in the spectral range. The optical member comprises an extraordinary dispersion optical material. The optical member comprises an optical doublet.

Advantages may include one or more of enabling high-quality endoscopic imaging of colors in an extended spectral range, supporting the use of a high-definition video camera in an endoscopic system, and correcting for chromatic aberrations in an endoscopic system throughout a spectral range imaged by a high-definition video camera.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a cutaway perspective view of an optical device is corrected for chromatic aberrations shown inserted into a body.

FIG. 9 is a cross-sectional view of an objective group of the optical system of FIG. 6.

FIG. 10 is a cross-sectional view of a first relay group of the optical system of FIG. 6.

FIG. 11 is a cross-sectional view of a second relay group of the optical system of FIG. 6.

FIG. 12 is a cross-sectional view of a third relay group of the optical system of FIG. 6.

DETAILED DESCRIPTION

Figure 1B:
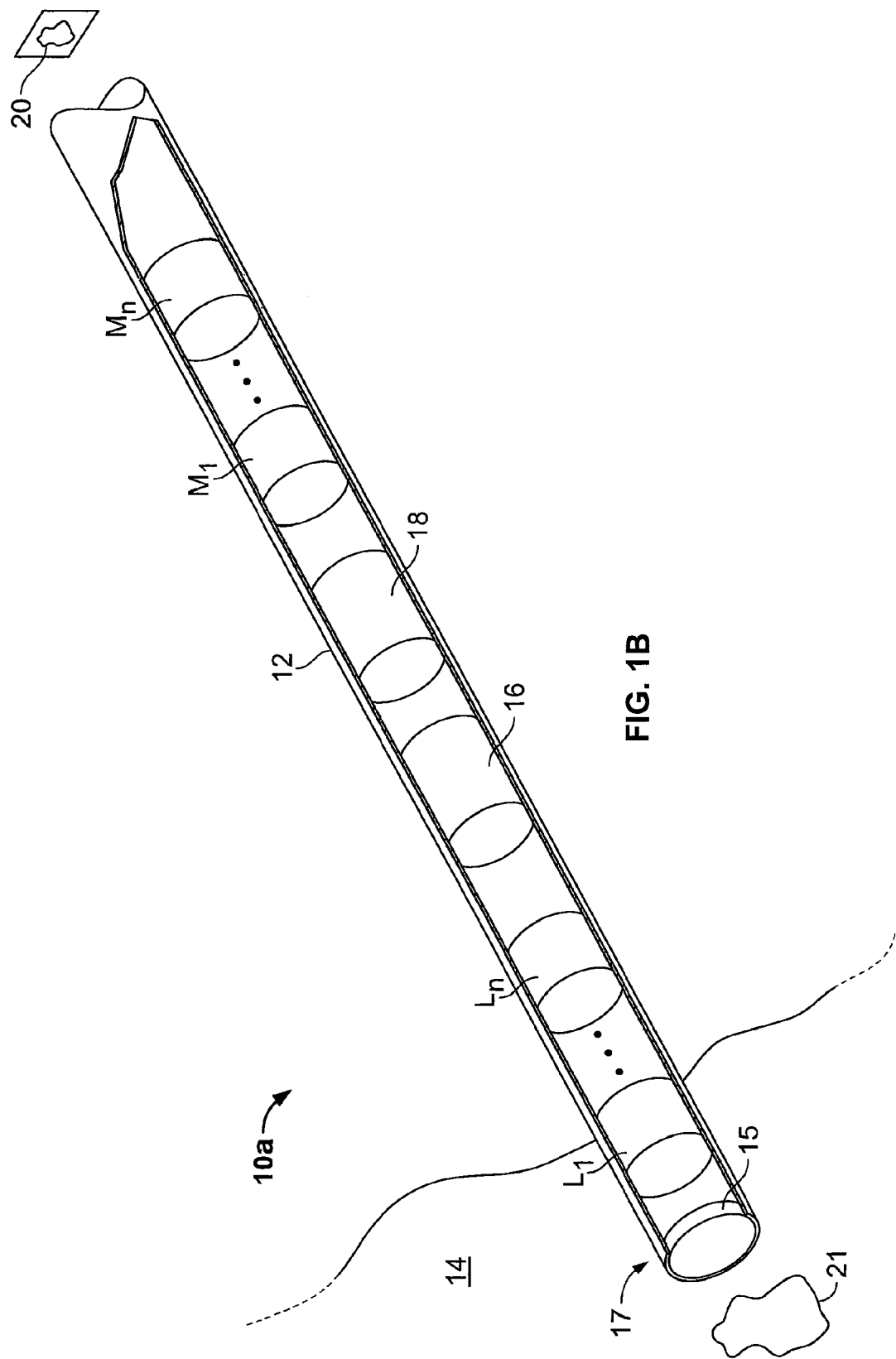
FIG. 1B is a cutaway perspective view of another implementation of the optical device.

Referring to FIG. 1A, an optical device 10 includes an elongated tube 12 configured for insertion into a body 14, an objective member 15 at an insertion end 17 of the tube 12, and first and second optical members 16, 18 located in the tube 12. The materials of the first optical member 16 and the second optical member 18 are selected to provide certain optical properties, for example, refractive indexes, that correct, or compensate, for chromatic aberrations in an image 20 of an object 21 in a spectrum of light extending beyond a conventional visible spectral range, for example, a range of wavelengths extending below about 480 nm or above about 644 nm, preferably below about 450 nm or about 650 nm. For example, an implementation of the optical device 10 includes an optical member formed of extraordinary dispersion optical materials and corrects for chromatic aberrations throughout an extended spectral range from about 435.8 nm to about 656.3 nm.

Referring to FIG. 1B, another implementation of an optical device 10a includes an elongated tube 12, as discussed above with reference to FIG. 1A, configured for insertion into a body 14. The optical device 10a has an objective member 15 at an insertion end 17 of the tube 12, and first and second optical members 16, 18 located in the tube 12. Each of the first and second optical members 16, 18 is formed of an extraordinary dispersion optical material. One or more additional optical members $L_1$-$L_n$ are located in the tube 12 between the objective member 15 and the first and second optical members 16, 18, and one or more additional optical members $M_1$-$M_n$ are located in the tube 12 on the opposite side of the first and second optical members 16, 18. The first and second optical members 16, 18 correct for chromatic aberrations caused by all of the optical members 15, 16, 18, $L_1$-$L_n$, M1-Mn throughout an extended spectral range from about 435.8 nm to about 656.3 nm.

Figure 2:
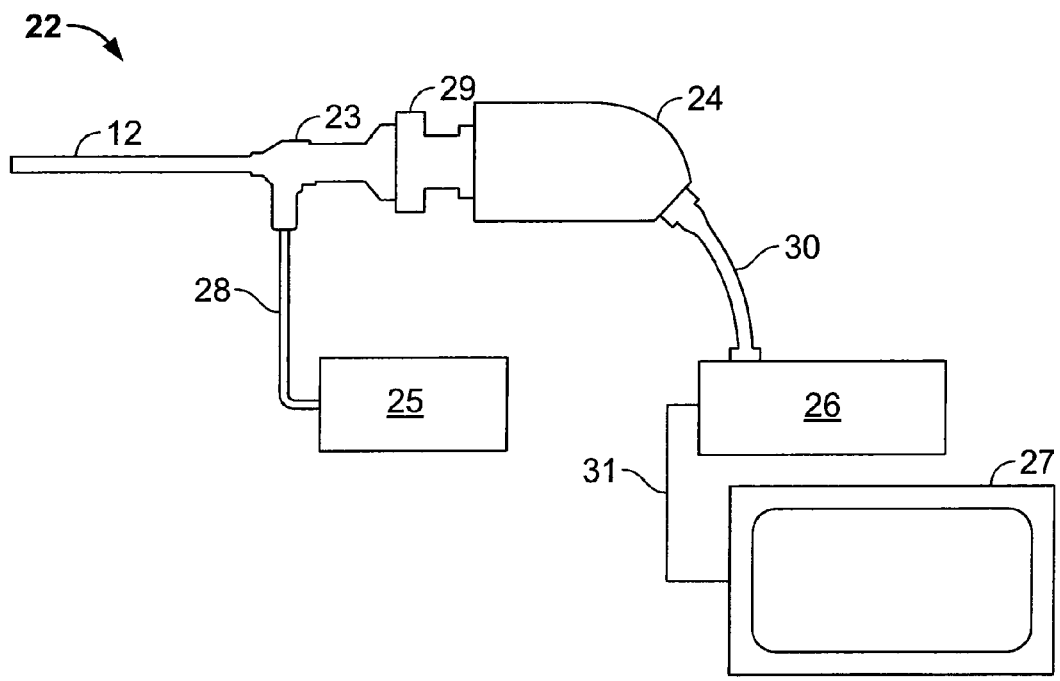
FIG. 2 illustrates an endoscopic system including the optical device of FIG. 1A.

As depicted in FIG. 2, a representative endoscopic system 22 includes an endoscope 23 with an elongated tube 12 for insertion into a body, an imaging device 24 such as a video camera head, a light source 25, an image processor 26 such as a camera control unit, and a display 27. The light source 25 is coupled to the endoscope 23 by an optical link 28, for example, a fiber optic cable, to illuminate the object 21 under observation (see FIG. 1). In addition, the imaging device 24 is optically coupled to the endoscope 23 by a coupler 29 to receive the image 20 (see FIG. 1), and electrically coupled to the image processor 26 by an electrical link 30 to transmit raw image data. The image processor 26 performs signal processing to produce a video signal, which is then transmitted by way of another electrical link 31 for display on the display 27, such as a cathode ray tube (CRT) display, a flat panel liquid crystal display (LCD) or plasma display panel (PDP), or any other suitable display device.

In some implementations, the imaging device 24 includes a high-definition video camera, although the imaging device 24 can include a standard-definition video camera or other suitable analog or digital camera. In general, color video cameras separately image blue, green and red spectra after these are divided by a color separation system. Given the spectra of the color bands imaged in typical high-definition video cameras, an optical device that is color-corrected in the extended spectral range is particularly useful in a high-definition video endoscopic system.

Figure 3:
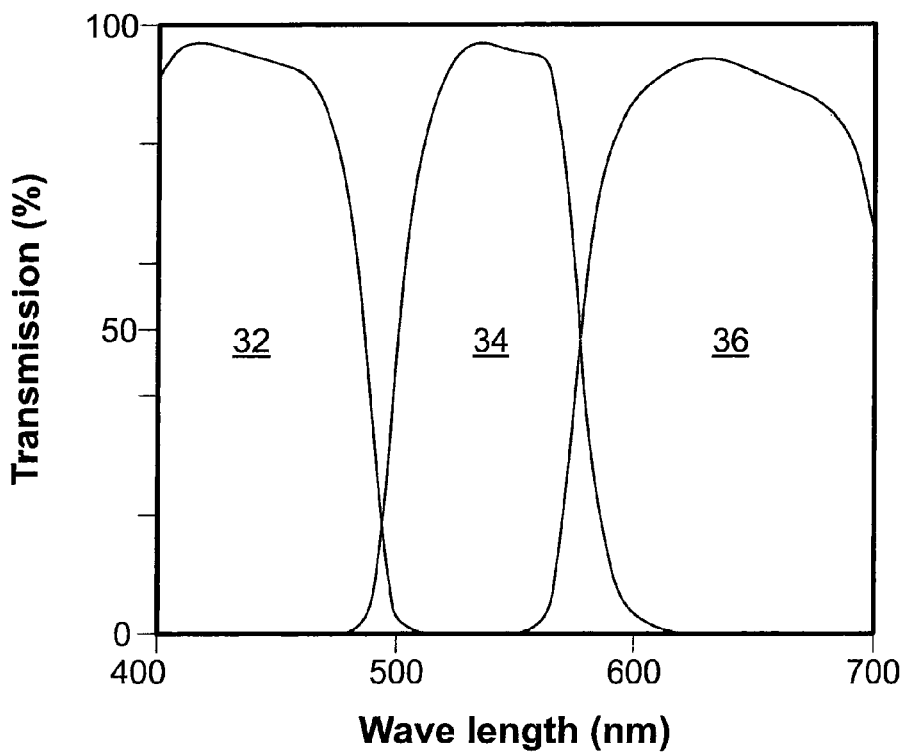
FIG. 3 is a graph illustrating color separation in a three-chip high-definition video camera.

The spectral characteristics of a typical high-definition video camera color separation system are shown in FIG. 3. The three separated wave bands corresponding to the blue spectral band 32, the green spectral band 34 and the red spectral band 36 are centered around approximately 440 nm, 55 nm and 650 nm. When imaged using a conventionally color-corrected endoscope, the extension into the blue color spectrum below 480 nm, in particular, results in substantial degradation of optical performance, because the refractive indexes of most optical materials increase rapidly as wavelength decreases through the blue color spectrum. Thus, the optical device 10 that is color-corrected in the extended spectral range from about 435.8 to about 656.3 nm enables higher quality video imaging, compared to that of a system that is color-corrected in the conventional spectral range of about 480 nm to about 644 nm.

The optical performance of the optical device 10 is substantially dependent on the following design criteria:

1) clear aperture diameter of the optical train;
2) light efficiency;
3) resolution and contrast.

The optical train diameter is limited by the external diameter of the insertion portion of the endoscope 23. The light energy transmitted through the optical device 10, i.e., the light efficiency of the device, is proportional to the square of the optical invariant, I, according to the following equation:

$$W = kI^2 \qquad (1)$$

In equation (1), W is the light energy transmitted through optical train, and k is a proportionality coefficient. Thus, to the extent that it is practical given the clear aperture semidiameter of the optical device 10, to provide maximum light efficiency the optical invariant of the optical device 10 is preferably maximized. The optical invariant is approximated by the following expression:

$$I = nH \sin U \qquad (2)$$

In equation (2), I is the optical invariant of the optical device 10, n is the refractive index of the image space medium, H is the image height (measured from the optical axis to full field), and U is the angle of the marginal ray with respect to the optical axis. In this approximation, numerical aperture (NA) is expressed as (n sin U), in accordance with the following equation:

$$NA = n \sin U \qquad (3)$$

For optical systems having air or evacuated space as the image space medium, the refractive n is equal to one (1). Without loss of generality, throughout this disclosure the refractive index n will be assumed to be equal to one.

The F-number, F#, of the optical device 10 can be expressed by the following equation:

$$F\# = \frac{1}{2NA} = \frac{1}{2\sin U} \quad (4)$$

Furthermore, relatively larger-diameter optical devices generally have a greater optical invariant value, generally resulting in better optical performance compared to relatively smaller-diameter optical devices. Some surgical procedures require endoscopes having a relatively small-diameter insertion portion, which conflicts with the design goal of maximizing light efficiency, resolution and contrast. Thus, a performance metric M is introduced in this disclosure to take into consideration both the optical invariant and the diameter of an optical device according to the following equation:

$$M = \frac{I}{D} \quad (5)$$

In equation (5), I is the optical invariant of the optical device, and D is the clear aperture semidiameter of the optical train. The performance metric M can be used as a substantially size-neutral comparison of optical performance for endoscopes of different diameters.

Empirical data based on endoscopes having diameters from about 1.5 millimeters (mm) to about 10 mm demonstrates that the performance metric M typically falls within the following range:

$$M \leftrightarrow (0.05\text{-}0.065) \quad (6)$$

Endoscopes in this size range having performance metric m values lower than approximately 0.05 have limited commercial value, and generally are not suitable for high-definition imaging applications.

Regarding resolution and contrast, for an ideal, diffraction-limited system the limiting resolution, or cut-off frequency $V_c$, is given by the following equation:

$$V_c = \frac{2}{\lambda}\sin U \quad (7)$$

In equation (7), $\lambda$ is the wavelength of the transmitted light, and the object is assumed to be a sinusoidal target. Thus, the theoretical maximum number of cycles per field, $N_{dl}$, that can be transmitted by the optical device 10 is given by the following equation:

$$N_{dl} = 2HV_c = (2\sin U)\frac{2H}{\lambda} = \frac{4I}{\lambda} \quad (8)$$

Equation (8) demonstrates that the number of resolved elements in an image is directly proportional to the optical invariant I of the optical device 10. Current high-definition television standards define two formats: 1) 1280×720, and 2) 1920×1080. Thus, depending on the format, a high-definition endoscopic imaging system displays 720 or 1080 lines per image height. In general, the optical device 10 preferably has an image resolution that exceeds the format specification.

The standard accepted criterion for defining diffraction-limited optical performance is the Rayleigh criterion, or limit. The Rayleigh criterion permits an optical path difference (OPD) of not more than one-quarter wavelength (¼λ) between the wavefront emerging from the optical device 10 and a reference sphere centered at a given image point. The vertex of the reference sphere generally is located in the exit pupil plane of the optical device 10. The Rayleigh criterion applies to all image points within the field of view of the optical device 10, as well as all wavelengths within the intended spectral range of the optical device 10.

Equation (8) can be rewritten as follows:

$$N_{dl} = \frac{I}{\frac{1}{4}\lambda} \quad (9)$$

The physical meaning of equation (9) is that the maximum theoretically-possible number of cycles per field for the optical device 10 will be reached when OPD meets the Rayleigh criterion of ¼λ.

Taking this into account, acceptance criteria for endoscopic optical systems can be specified. For instance, with an increase in diameter and accompanying increase in the optical invariant I, the maximum number of cycles/field undergoes a proportional increase, allowing optical performance with OPD greater than one-quarter wave. Thus, for example, to support high-definition imaging with 720 TV lines:

$$OPD \leq \frac{I}{360\lambda} \quad (10)$$

This criterion applies to optical systems having relatively large values of the optical invariant I, such that the OPD calculated in equation (10) is not less than ¼λ. On the other hand, if the optical invariant I value is sufficiently low that I/(360λ) is less than one quarter, then the optical system is intrinsically incapable of supporting high-definition imaging with 720 TV lines. In general, there is no reason to improve an optical system beyond the OPD=¼λ level, since at this point the system is limited by diffraction effects, and further correction for aberrations does not improve the image quality, but rather, only adds unnecessary expense to the cost of the optical system.

For example, an optical system that provides sufficient resolution and contrast across an acceptable field of view to support high-definition imaging with 720 lines preferably complies with equation (11) and either equation (12a) or (12b) as follows:

$$M \geq 0.05 \quad (11)$$

$$\frac{1}{4} \leq OPD \leq \frac{I}{360\lambda} \quad (12a)$$

$$OPD \leq \frac{1}{4} \quad (12b)$$

In equation (12a), $\lambda$ is a reference wavelength, for example, a midrange wavelength approximately in the center of the design range, such as 546 nm for visible light, based on the green mercury line e. The criteria of equations (11), (12a), and (12b) generally apply to all wavelengths in the design range, and to all the image points across the entire field of view of the optical system.

Image resolution and contrast are substantially dependent on the degree to which chromatic aberrations are corrected in the optical system. The modulation transfer function (MTF) is a measure of the contrast to which detail in an object 21 is reproduced in an image 20. The diffraction-limited MTF curve represents a measure of the perfect or aberration-free image. Polychromatic MTF curves include the effect of any chromatic aberrations that may be present in an image produced by the optical system.

Figure 4:
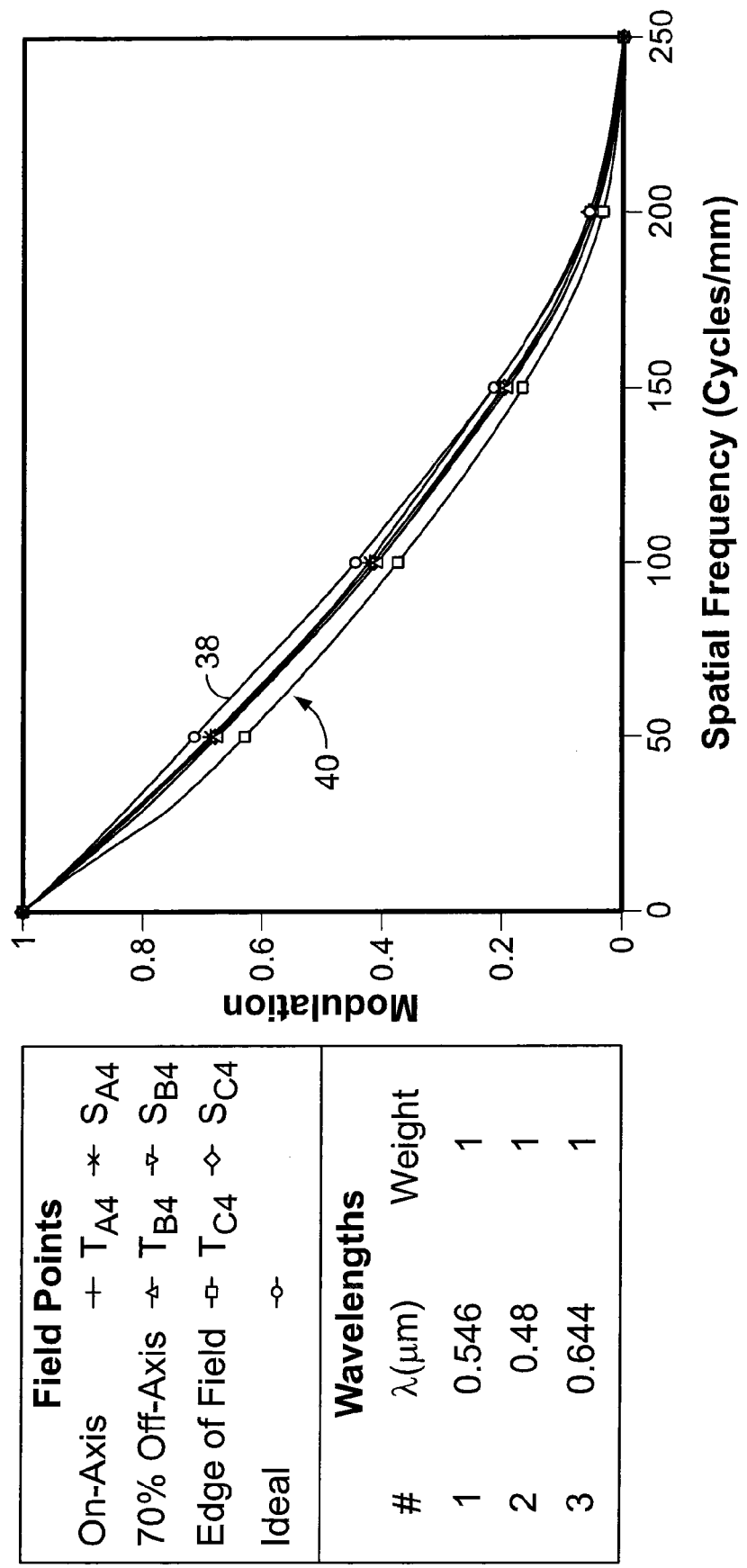
FIG. 4 is a graph illustrating an ideal modulation transfer function (MTF) and polychromatic MTF curves of a prior art optical device that is color-corrected in a standard visible spectral range.
Figure 8:
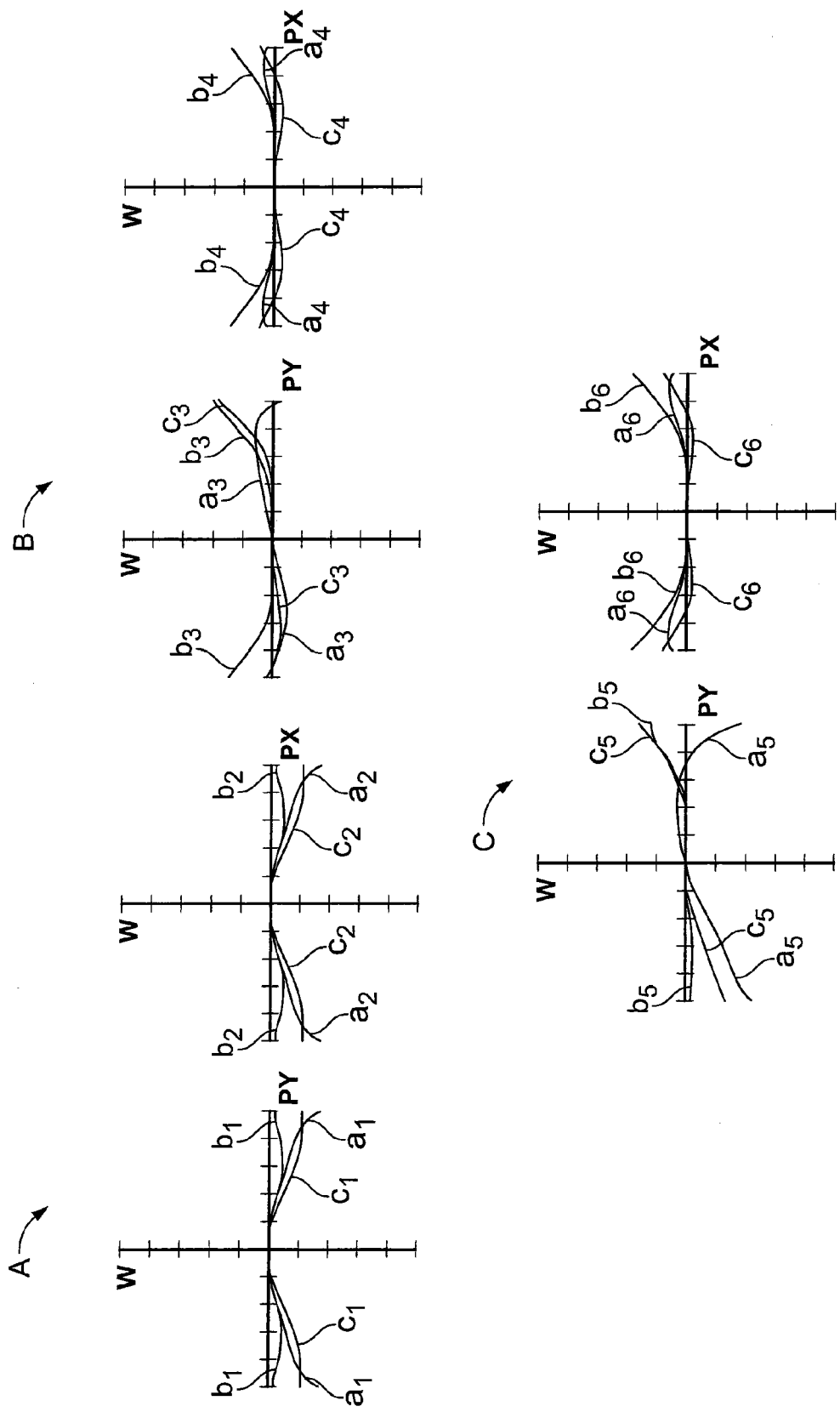
FIG. 8 is a set of graphs illustrating optical path differences at the image plane of the optical device of FIG. 6.
Figure 13:
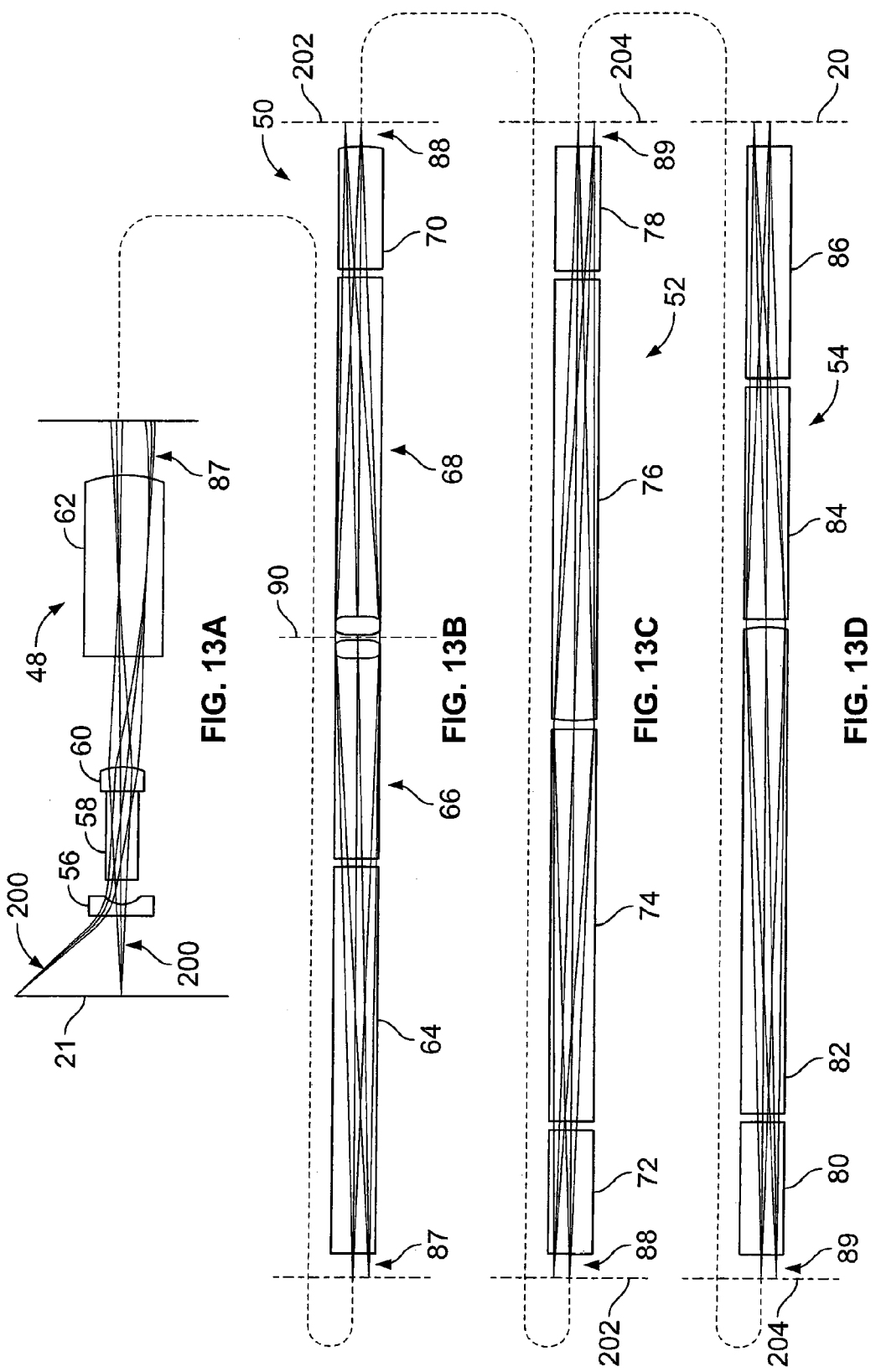
FIGS. 13A-D are an optical schematic illustrating the optical device of FIG. 6.

FIG. 4 shows an ideal MTF curve 38 and polychromatic MTF curves 40 for an optical system corrected for chromatic aberrations in a spectral range from about 480 nm to about 644 nm, such as that disclosed in U.S. Pat. No. 6,853,485 to Hoogland, entitled "Integrated Optical System for Endoscopes and the Like," issued on Feb. 8, 2005, the disclosure of which is hereby incorporated by reference in its entirety. The polychromatic MTF curves 40 are shown for light rays at the optical axis, 70% off-axis, and off-axis full field, or edge of field (EOF), based on the discrete wavelengths of 480 nm, 546 nm and 644 nm with equal weighting in a spatial frequency range from zero to 250 cycles per millimeter (cycles/mm). The curves $T_{A4}$, $S_{A4}$ are the MTF curves in the coincidental tangential and sagittal planes at the optical axis; $T_{B4}$ is the MTF curve in the tangential plane and $S_{B4}$ is the MTF curve in the sagittal plane at 70% off axis; and $T_{C4}$ is the MTF curve in the tangential plane and $S_{C4}$ the MTF curve in the sagittal plane at the edge of field. As can be seen in FIG. 8, the values of all of the MTF curves of the polychromatic MTF curves 40 substantially conform to the ideal MTF curve 38, representing a color-corrected image.

Figure 5:
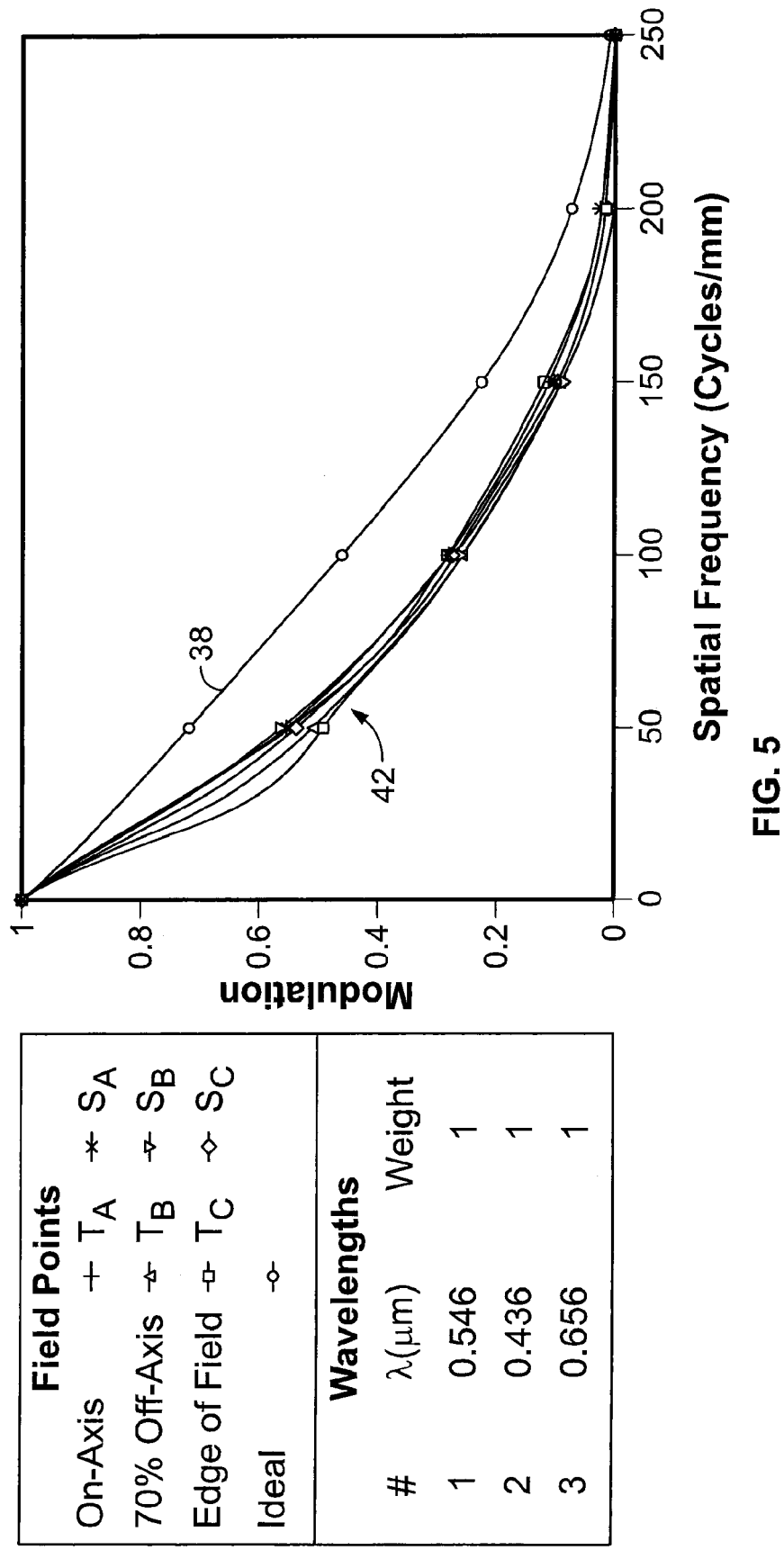
FIG. 5 is a graph illustrating the ideal MTF curve and polychromatic MTF curves of the prior art optical device represented in FIG. 4 in an extended spectral range.

However, for the same optical system, FIG. 5 shows the ideal MTF curve 38 and polychromatic MTF curves 42 in the extended spectral range based on the discrete wavelengths of 436 nm, 546 nm and 656 nm with equal weighting. As can be seen in FIG. 5, the polychromatic MTF curves 42 are substantially degraded.

Figure 6:
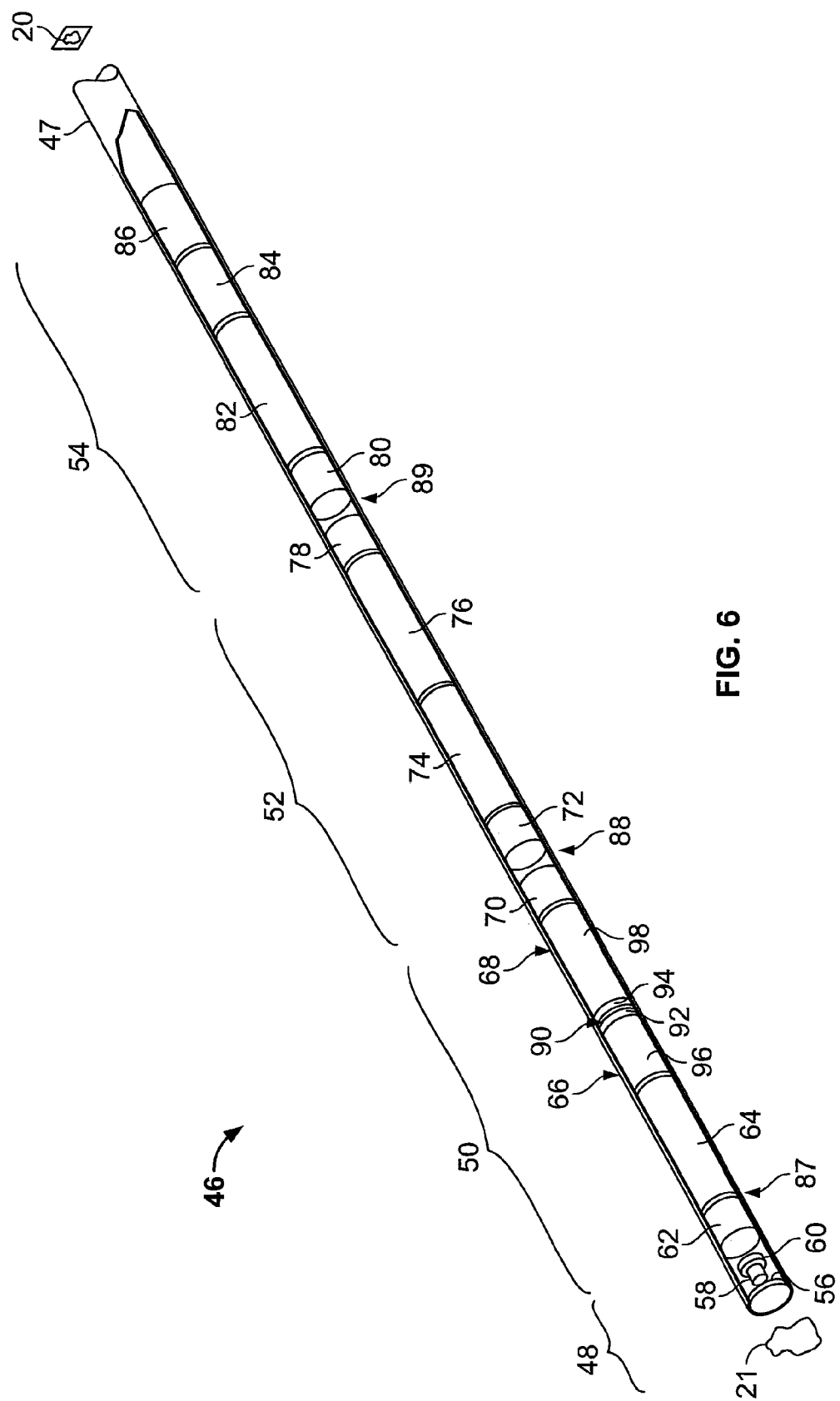
FIG. 6 is a cutaway perspective view of an implementation of an optical device that is color-corrected in the extended spectral range for use in a rigid endoscope.
Figure 7:
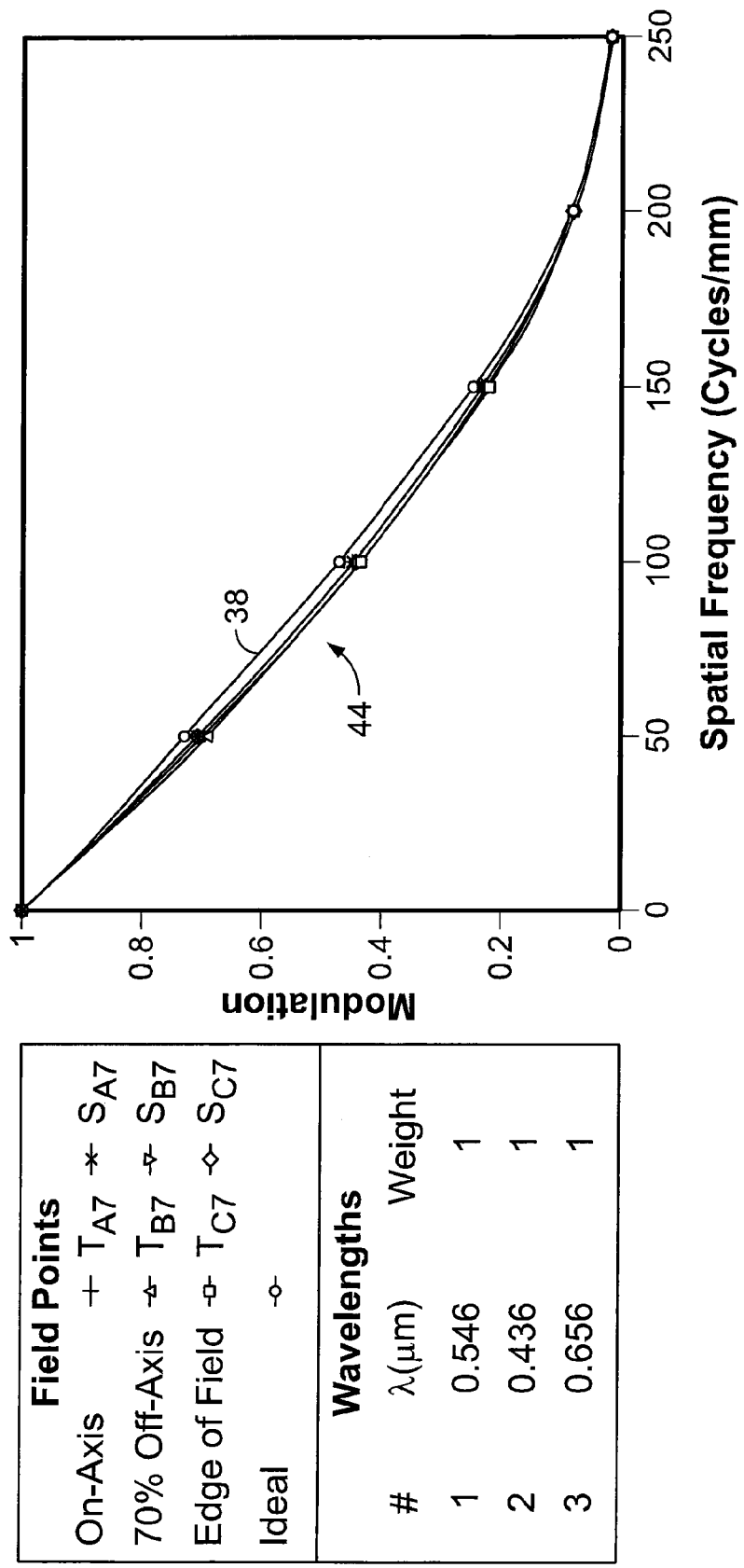
FIG. 7 is a graph illustrating the ideal MTF curve and polychromatic MTF curves of the optical device of FIG. 6 in the extended spectral range.

In contrast, referring to FIGS. 6 and 7, the values of all of the polychromatic MTF curves 44 for an optical device 46 that corrects for chromatic aberrations in the range of about 435.8 nm to about 656.3 nm substantially conform to the ideal MTF curve 38. The polychromatic MTF curves 44 is shown for light rays at the optical axis, 70% off-axis, and at the EOF based on the discrete wavelengths of 436 nm, 546 nm and 656 nm with equal weighting in a spatial frequency range from zero to 250 cycles per millimeter (cycles/mm).

The curves $T_{A7}$, $S_{A7}$ are the MTF curves in the coincidental tangential and sagittal plane at the optical axis; $T_{B7}$ is the MTF curve in the tangential plane and $S_{B7}$ is the MTF curve in the sagittal plane at 70% off axis; and $T_{C7}$ is the MTF curve in the tangential plane and $S_{C7}$ the MTF curve in the sagittal plane at the edge of field. Thus, the optical performance of optical device 46 is nearly diffraction-limited in the spectral band from about 435.8 nm to about 656.3 nm, facilitating higher quality video imaging, which is advantageous when used in conjunction with a three-chip color video camera, and particularly with a high-definition video camera.

Applying the above criteria, the optical device 46 has sufficient optical performance to support high-definition imaging. For the optical device 46, image height H=1.17 mm, and the marginal ray angle U=3.59°. Thus, from equation (2), the optical invariant I=0.073, the clear aperture semidiameter D=1.25 mm (see Table 2 below). From equation (5), the performance metric M=0.0586. Thus, the optical device 46 meets the criterion M≧0.05. Equation (8) yields the cut-off resolution $N_{di}$=535 cycles/image, which corresponds to 1,070 lines per sensor/monitor height. (As is customary, the reference wavelength λ=546 nm was used in this calculation, based on the green mercury line e, which is representative of the visible range of light.)

In addition, FIG. 8 graphically illustrates the optical path differences of the optical device 46 for the discrete wavelengths of 436 nm (a), 546 nm (b) and 656 nm (c) at the optical axis (A), 70% off axis (B), and off axis full field, or edge of field [EOF] (C), in the tangential (PY) and sagittal (PX) planes. The curves $a_1$, $b_1$, $c_1$ represent the on-axis optical path differences in the tangential plane corresponding to wavelengths of 436 nm, 546 nm and 656 nm, respectively; and the curves $a_2$, $b_2$, $c_2$ represent the on-axis optical path differences in the sagittal plane corresponding to wavelengths of 436 nm, 546 nm and 656 nm, respectively. The curves $a_3$, $b_3$, $c_3$ represent the 70% off-axis optical path differences in the tangential plane, and the curves $a_4$, $b_4$, $c_4$ the 70% off-axis optical path differences in the sagittal plane, corresponding to wavelengths of 436 nm, 546 nm and 656 nm, respectively. The curves $a_5$, $b_5$, $c_5$ represent the EOF optical path differences in the tangential plane, and curves $a_6$, $b_6$, $c_6$ represent the EOF optical path differences in the sagittal plane, corresponding to wavelengths of 436 nm, 546 nm and 656 nm, respectively.

As can be seen in FIG. 8, the OPD curves for the optical device 46 computed for three wavelengths at the low, middle and high limits, respectively, of the extended spectral range are contained within about ¼λ at most points, and thus, the optical device 46 substantially meets the Rayleigh criterion for diffraction-limited optical performance.

Referring to FIG. 6, the optical device 46 includes an elongated tube 47, for example, between about 50 mm and about 450 mm in length, configured for insertion into a body. Located in the tube 47 are an objective group 48, a first relay group 50, a second relay group 52, and a third relay group 54 of lenses axially aligned along an optical axis to transmit light from the object 21 to the image 20.

The objective group 48 includes a field-expanding lens 56, a direction of view prism 58 (represented in FIG. 6 as a plano-plano rod with equivalent optical path length), a lens 60 and a rod lens 62. In addition, the first relay group 50 includes a rod lens 64, two doublets 66, 68 and an additional rod lens 70. Furthermore, the second relay group 52 includes four rod lenses 72, 74, 76, 78. Similarly, the third relay group 54 includes four rod lenses 80, 82, 84, 86. The objective group 48 is spaced apart from the first relay group 50 by a gap 87, the first relay group 50 is spaced apart from the second relay group 52 by a gap 88, and the second relay group 52 is spaced apart from the third relay group 54 by a gap 89.

The doublets 66, 68, which are located on either side of a pupil plane 90 (a conjugate to the exit and entrance pupil planes) perform most of the compensation for chromatic aberrations in the optical device 46. Each of the doublets 66, 68 includes a lens 92, 94 bonded to a rod lens 96, 98, respectively, with the doublet 68 in an opposed configuration with regard to that of the doublet 66. In order to correct for chromatic aberrations in an extended spectral range, for example, from about 435.8 nm to about 656.3 nm, the two lenses 92, 94 are composed of one extraordinary dispersion optical material, and the two rod lenses 96, 98 are composed of a different extraordinary dispersion optical material.

Referring to FIG. 9, the field-expanding lens 56 is a plano-concave lens made of an optical material, such as optical glass, sapphire, or the like, having planar surface 100 and concave surface 102. The direction of view prism 58 is modeled herein as a plano-plano rod lens having two planar surfaces 104, 106. The direction of view prism 58 is bonded to the objective lens 60, which is a plano-convex lens made of optical glass having a planar surface 108 and a convex surface 110. The rod lens 62 is a plano-convex rod lens made of optical glass having a planar surface 112 and a convex surface 114. In addition, the field-expanding lens 56 is spaced apart from the direction of view prism 58 by a gap 116, and the objective lens 60 is spaced apart from the rod lens 62 by a gap 118.

As shown in FIG. 10, the lens 64 of the first relay group 50 is a plano-plano rod lens made of optical having a planar surface 122 and a planar surface 124. The lens 96 is a plano-concave rod lens made of extraordinary dispersion optical material having a planar surface 126 and a concave surface 128. In addition, the lens 92 is a biconvex lens made of extraordinary dispersion optical material having two convex surfaces 130, 132. The surface 130 of lens 92 is bonded to surface 128 of rod lens 96 to form the doublet 66. Similarly, the lens 94 is a biconvex lens made of extraordinary dispersion optical material having two convex surfaces 134, 136, the lens 98 is a plano-concave rod lens made of extraordinary dispersion optical material having a concave surface 138 and a planar surface 140, and the surface 136 of the lens 94 is bonded to the surface 138 of the rod lens 97 to form the other doublet 68. Furthermore, the lens 70 of the first relay group 50 is a plano-convex rod lens made of optical glass having a planar surface 142 and a convex surface 144. Moreover, the lens 64 is spaced apart from the lens 96 by a gap 146, the lens 92 is spaced apart from the lens 94 by a gap 148, and the lens 98 is spaced apart from the lens 70 by a gap 150. The surfaces of the lenses are bonded by gluing the surfaces with optical glue. However, air-space doublet configurations also may be used.

Referring to FIG. 11, the lens 72 of the second relay group 52 is a plano-convex rod lens made of optical glass having a convex surface 152 and a planar surface 154. The lens 74 is a plano-plano rod lens made of optical glass having two planar surfaces 156, 158. In addition, the lens 76 is a plano-convex rod lens made of optical glass having a convex surface 160 and a planar surface 162. Furthermore, the lens 78 is a plano-convex rod lens made of optical glass having a planar surface 164 and a convex surface 168. Moreover, the lens 72 is spaced apart from the lens 74 by a gap 170, the lens 74 is spaced apart from the lens 76 by a gap 172, and the lens 76 is spaced apart from the lens 78 by a gap 174.

As shown in FIG. 12, the lens 80 of the third relay group 54 is a plano-convex rod lens made of optical glass having a convex surface 176 and a planar surface 178. The lens 82 is a plano-convex rod lens made of optical glass having a planar surface 180 and a convex surface 182. In addition, the lens 84 is a plano-plano rod lens made of optical glass having two planar surfaces 184, 186. Similarly, the lens 86 is a plano-plano rod lens made of optical glass having two planar surfaces 188, 190. Furthermore, the lens 80 is spaced apart from the lens 82 by a gap 192, the lens 82 is spaced apart from the lens 84 by a gap 194, and the lens 84 is spaced apart from the lens 86 by a gap 196.

Table 1 provides a detailed lens prescription describing an implementation of the optical device 46. Although the spaces between lenses have been specified as "air," in alternative implementations the spaces between lenses can include another gas that has a refractive index of about one (1) or a complete vacuum.

Referring to FIGS. 13A-D, in use, polychromatic light 200 from a plane of the object 21 is conducted through the objective group 48, where the field-expanding lens 56 permits a relatively wide field of view to be imaged, for example, from about 65 to about 125 degrees. The direction of view prism 58 transmits the light 200 to the objective lens 60.

The first relay group 50 relays the light 200 to a intermediate image plan 202 in the gap 88 between the first and second relay groups 50, 52. The extraordinary dispersion optical doublets 66, 68 correct for chromatic aberrations caused by the entire lens train, including the objective group 48 and the three relay groups 50, 52, 54, in a spectral range from about 435.8 nm to about 656.3 nm. The second relay group 52 relays the light to a intermediate image plane 204 in the gap 89 between the second and third relay groups 52, 54, and the third relay group 54 relays the light 200 to the plane of the image 20. In this manner, the light 200 is transmitted from the object 21 to the image 20 and is color-corrected for high-quality imaging substantially free of chromatic aberrations, for example, by a high-definition video camera.

Other implementations are within the scope of the following claims. For example, in one implementation, extraordinary dispersion optical material doublets are placed in the third relay, instead of in the first relay as described above. Table 2 provides a detailed lens prescription describing this implementation of an optical device.

TABLE 1

Lens Prescription for an Implementation of an Optical System

| Reference No. | Surface No. | Radius (mm) | Thickness (mm) | Semidiameter (mm) | Medium (material) |
|---|---|---|---|---|---|
| N/A | 0 | N/A | 8.000 | 10.426 | air |
| 100 | 1 | infinity | 0.300 | 1.100 | SAPPHIRE |
| 102 | 2 | 0.68 | 0.800 | 0.564 | air |
| 104 | 3 | infinity | 2.535 | 0.535 | S-TIH6 |
| 106/108 | 4 | infinity | 0.725 | 0.535 | S-LAH55 |
| 110 | 5 | −1.652 | 3.154 | 0.723 | air |
| 112 | 6 | infinity | 5.357 | 1.250 | S-LAL18 |
| 114 | 7 | −4.08 | 0.298 | 1.250 | air |
| 122 | 8 | infinity | 20.661 | 1.250 | S-LAH55 |
| 124 | 9 | infinity | 0.495 | 1.250 | air |
| 126 | 10 | infinity | 10.088 | 1.250 | N-KZFS11 |
| 128/130 | 11 | 4.26 | 1.200 | 1.250 | S-FPL53 |
| 132 | 12 | −4.26 | 0.145 | 1.250 | air |
| 134 | 13 | 5.04 | 1.200 | 1.250 | S-FPL53 |
| 136/138 | 14 | −3.93 | 18.000 | 1.250 | N-KZFS11 |
| 140 | 15 | infinity | 0.495 | 1.250 | air |
| 142 | 16 | infinity | 6.500 | 1.250 | S-BSL7 |
| 144 | 17 | −8.94 | 2.016 | 1.250 | air |
| N/A | 18 | infinity | 2.016 | 1.250 | air |
| 152 | 19 | 8.94 | 6.500 | 1.250 | S-BSL7 |
| 154 | 20 | infinity | 0.500 | 1.250 | air |
| 156 | 21 | infinity | 20.661 | 1.250 | S-LAH55 |
| 158 | 22 | infinity | 0.391 | 1.250 | air |
| 160 | 23 | 7.7 | 23.149 | 1.250 | S-LAH66 |
| 162 | 24 | infinity | 0.500 | 1.250 | air |
| 164 | 25 | infinity | 6.500 | 1.250 | S-BSL7 |
| 168 | 26 | −8.94 | 2.012 | 1.250 | air |
| N/A | 27 | infinity | 2.012 | 1.250 | air |
| 176 | 28 | 8.94 | 6.500 | 1.250 | S-BSL7 |
| 178 | 29 | infinity | 0.495 | 1.250 | air |
| 180 | 30 | infinity | 23.149 | 1.250 | S-LAH66 |
| 182 | 31 | −7.7 | 0.392 | 1.250 | air |
| 184 | 32 | infinity | 11.105 | 1.250 | S-BSL7 |
| 186 | 33 | infinity | 0.500 | 1.250 | air |
| 188 | 34 | infinity | 11.105 | 1.250 | S-BSL7 |
| 190 | 35 | infinity | 3.600 | 1.250 | air |
| N/A | 36 | infinity | N/A | 1.171 | air |

Figure 14:
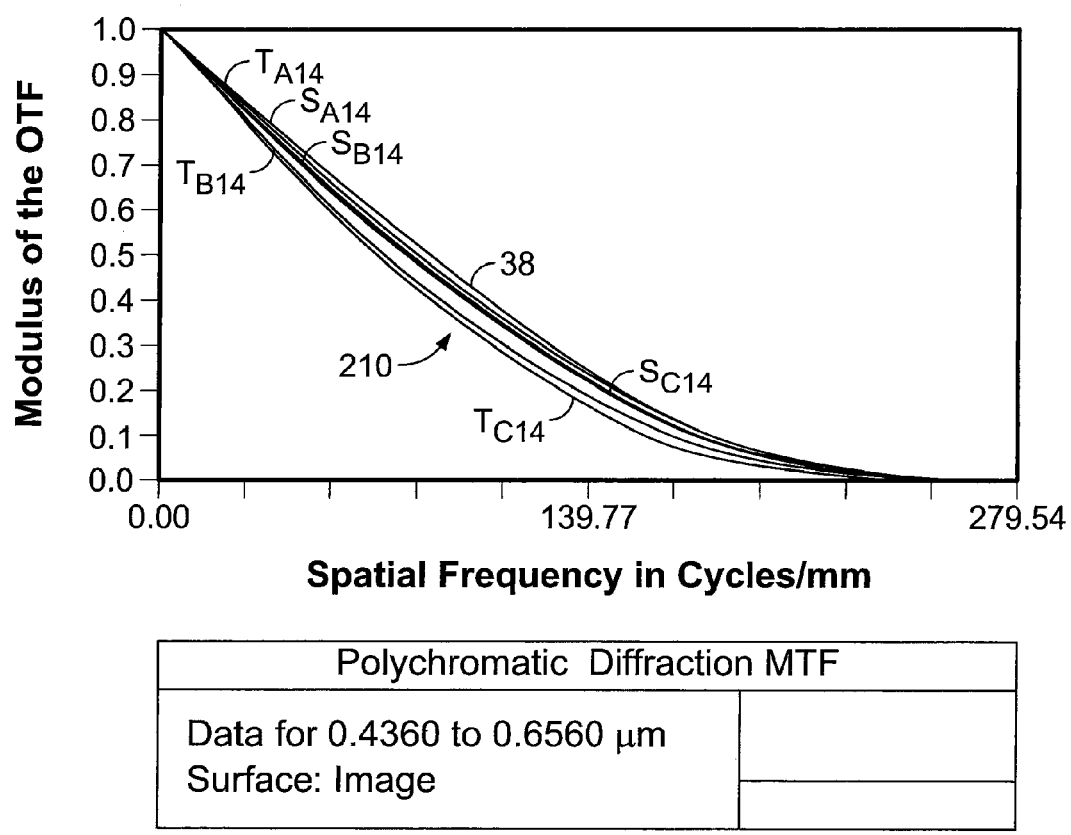
FIG. 14 is a graph illustrating the ideal MTF curve and polychromatic MTF curves of another implementation of the optical device that is color-corrected in the extended spectral range for use in a rigid endoscope.

FIG. 14 shows the corresponding polychromatic MTF curves 210 in an extended spectral range at the optical axis (A), 70% off axis (B), and off axis full field (C), or edge of field (EOF), based on the discrete wavelengths of 436 nm, 546 nm and 656 nm with equal weighting in a spatial frequency range from zero to 250 (cycles/mm). The curves $T_{A14}$, $S_{A14}$ are the MTF curves in the coincidental tangential and sagittal planes at the optical axis; $T_{B14}$ is the MTF curve in the tangential plane and $S_{B14}$ is the MTF curve in the sagittal plane at 70% off axis; and $T_{C14}$ is the MTF curve in the tangential plane and $S_{C14}$ the MTF curve in the sagittal plane at the edge of field. As can be seen in FIG. 14, the values of all of the MTF curves of the polychromatic MTF curves 210 substantially conform to the ideal MTF curve 38.

Figure 15:
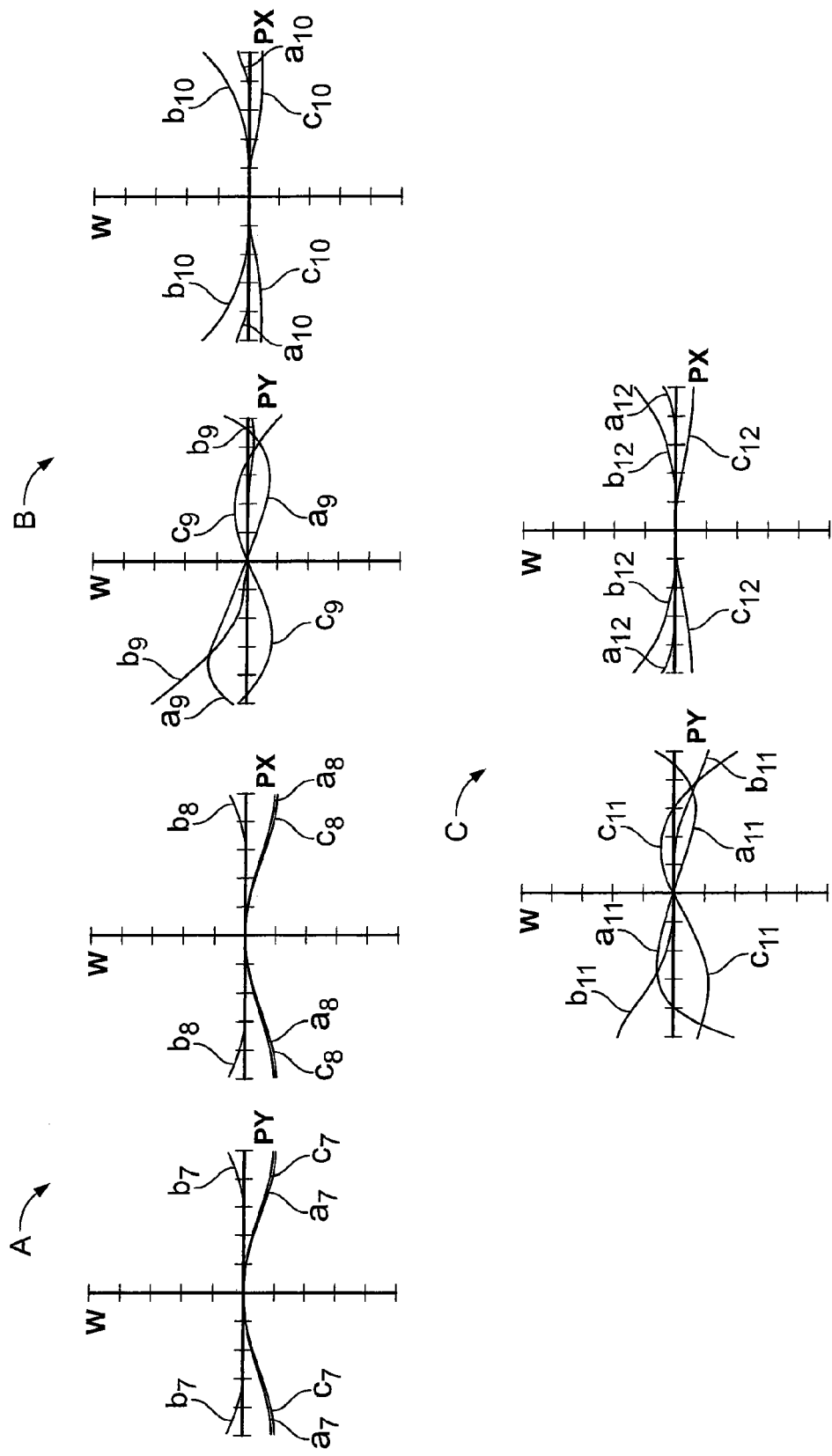
FIG. 15 is a set of graphs illustrating optical path differences at the image plane of the optical device of FIG. 14.

In addition, FIG. 15 graphically illustrates the corresponding optical path differences for the discrete wavelengths of 436 nm (a), 546 nm (b) and 656 nm (c) at the optical axis (A), 70% off axis (B), and at the edge of field (C) in the tangential (PY) and sagittal (PX) planes. The curves $a_7$, $b_7$, $c_7$ represent the on-axis optical path differences in the tangential plane, and curves $a_8$, $b_8$, $c_8$ the on-axis optical path differences in the sagittal plane, corresponding to wavelengths of 436 nm, 546 nm and 656 nm, respectively. The curves $a_9$, $b_9$, $c_9$ represent the 70% off-axis optical path differences in the tangential plane, and the curves $a_{10}$, $b_{10}$, $c_{10}$ the 70% off-axis optical path differences in the sagittal plane, corresponding to wavelengths of 436 nm, 546 nm and 656 nm, respectively. The curves a11, b11, c11 represent the EOF optical path differences in the tangential plane, and curves a12, b12, c12 the EOF optical path differences in the sagittal plane, corresponding to wavelengths of 436 nm, 546 nm and 656 nm, respectively.

As in the previous implementation, the OPD curves computed for three wavelengths at the low, middle and high limits, respectively, of the extended spectral range are contained within about ¼λ at most points, and thus, this implementation of the optical device substantially meets the Rayleigh criterion for diffraction-limited optical performance.

TABLE 2

Lens Prescription for Another Implementation of an Optical System

| Surface No. | Radius (mm) | Thickness (mm) | Medium (material) | Semidiameter (mm) |
|---|---|---|---|---|
| 0 | infinity | 8.00 | air | 10.426 |
| 1 | infinity | 0.30 | SAPPHIRE | 1.000 |
| 2 | 0.691 | 0.80 | air | 0.508 |
| 3 | infinity | 2.50 | S-NPH1 | 0.440 |
| 4 | infinity | 0.73 | S-YGH51 | 0.340 |
| 5 | −1.626 | 2.17 | air | 0.460 |
| 6 | infinity | 6.75 | S-YGH51 | 1.250 |
| 7 | −3.826 | 0.30 | air | 1.250 |
| 8 | 47.317 | 13.70 | S-NPH1 | 1.250 |
| 9 | 4.447 | 0.50 | air | 1.250 |
| 10 | 6.193 | 15.90 | S-YGH51 | 1.250 |
| 11 | −12.621 | 0.30 | air | 1.250 |
| 12 | 11.087 | 9.27 | S-YGH51 | 1.250 |
| 13 | infinity | 0.50 | air | 1.250 |
| 14 | infinity | 13.30 | S-YGH51 | 1.250 |
| 15 | 15.375 | 2.00 | air | 1.250 |
| 16 | infinity | 2.00 | air | 1.250 |
| 17 | 6.099 | 15.10 | S-YGH51 | 1.250 |
| 18 | infinity | 0.50 | air | 1.250 |
| 19 | infinity | 13.30 | S-YGH51 | 1.250 |
| 20 | infinity | 0.40 | air | 1.250 |
| 21 | 7.527 | 14.70 | S-YGH51 | 1.250 |
| 22 | infinity | 0.50 | air | 1.250 |
| 23 | infinity | 14.50 | S-YGH51 | 1.250 |
| 24 | −11.452 | 2.00 | air | 1.250 |
| 25 | infinity | 2.00 | air | 1.250 |
| 26 | 11.452 | 14.50 | S-YGH51 | 1.250 |
| 27 | infinity | 0.50 | air | 1.250 |
| 28 | infinity | 13.30 | N-KZFS11 | 1.250 |
| 29 | 6.884 | 1.40 | S-FPL52 | 1.250 |
| 30 | −5.560 | 0.50 | air | 1.250 |
| 31 | 5.909 | 2.00 | S-FPL52 | 1.250 |
| 32 | −3.721 | 11.30 | N-KZFS11 | 1.250 |
| 33 | −37.732 | 0.50 | air | 1.250 |
| 34 | infinity | 13.30 | S-YGH51 | 1.250 |
| 35 | infinity | 3.60 | air | 1.250 |
| 36 | infinity | 0.00 | air | 1.171 |

In other implementations, equation (12a) can be modified to accommodate other format specifications. For example, to support an endoscopic system using high-definition imaging with 1080 TV lines, the following criterion can be satisfied:

$$\frac{1}{4} \leq OPD = \frac{I}{540\lambda} \quad (13)$$

Similarly, any high-definition imaging format can be supported by modifying the criterion to correspond to the specified number of lines per image height.

In some implementations, it may be desirable to provide an optical system OPD below the upper limit, that is, closer to the diffraction limit of ¼λ, in order to provide an optical system with improved MTF. For example, if the optical invariant I is relatively large, such as for 10-mm diameter endoscopes, the number of resolvable cycles/field is also relatively large. In this case, OPD can be adjusted downward, and the system MTF continues to improve until OPD reaches the Rayleigh limit of ¼λ.

In an implementation of the optical system, the criteria of equations (11) and (12a) or (12b) are applied to the image points across a partial field of view, in which case the remainder (e.g., the periphery) of the field is allowed to have lower resolution and contrast.

In alternative implementations of the disclosed optical device, additional optical elements or components may be employed, such as a ocular lens, a coupling lens, a zoom lens system or additional relay groups. In addition, correction for chromatic aberrations may be incorporated in a different group, such as any of the relay groups.

It will be understood that various modifications may be made. For example, useful results still could be achieved if the components or techniques in the disclosed apparatus and methods were substituted or supplemented by equivalent or additional complementary components or techniques. Accordingly, other implementations are within the scope of the following claims.

What is claimed is:

1. A device, comprising:
an elongated tube configured for insertion into a body; and
at least two optical members located in the tube, wherein the optical members in combination are configured such that the device has an optical invariant-to-clear aperture semidiameter ratio greater than about 0.05, an optical path difference less than a value of the optical invariant divided by at least 250 times a midrange wavelength in a spectral range from about 435.8 to about 656.3 nanometers, wherein at least one of the optical members comprises an extraordinary dispersion optical material.

2. The device of claim 1, wherein the optical members in combination are configured such that the device has an optical path difference less than a value of the optical invariant divided by 320 times a midrange wavelength in the spectral range.

3. The device of claim 1, wherein the optical members in combination are configured such that the device has an optical path difference less than a value of the optical invariant divided by 450 times a midrange wavelength in the spectral range.

4. The device of claim 1, wherein the at least one optical member comprises a first extraordinary dispersion optical material and another of the optical members comprises a second different extraordinary dispersion optical material.

5. The device of claim 1, wherein at least one of the optical members comprises an optical doublet.

6. The device of claim 5, wherein a pair of optical doublets are adjacent opposite side of a pupil plane.

7. The device of claim 6, wherein each optical doublet comprises two lenses bonded to one another, and at least one of the lenses includes an extraordinary dispersion optical material.

8. The device of claim 6, wherein each optical doublet comprises a lens that includes an extraordinary dispersion optical material and another lens that includes a different extraordinary dispersion optical material.

9. The device of claim 8, wherein the extraordinary dispersion optical materials comprise N-KZFS11 and S-FPL53.

10. The device of claim 6, wherein each optical doublet comprises a plano-concave rod lens bonded to a biconvex lens.

11. The device of claim 10, wherein each optical doublet is axially aligned along an optical axis, the biconvex lenses being adjacent opposite sides of a pupil plane.

12. The device of claim 5, wherein the device further comprises an objective group and at least one relay group, and the relay group nearest the objective group includes the optical doublet.

13. The device of claim 5, wherein the device further comprises an objective group and at least one relay group, and the relay group most distant from the objective group includes the optical doublet.

14. A method, comprising:
conducting polychromatic light through at least two optical members of a device, the optical members being located in an elongated tube configured for insertion into a body, wherein the members in combination are configured such that the device has an optical invariant-to-clear aperture semidiameter ratio greater than about 0.05, an optical path difference less than a value of the optical invariant divided by at least 250 times a midrange wavelength in a spectral range from about 435.8 to about 656.3 nanometers, wherein at least one of the optical members comprises an extraordinary dispersion optical material.

15. The device of claim 14, wherein the optical members in combination are configured such that the device has an optical path difference less than a value of the optical invariant divided by 320 times a midrange wavelength in the spectral range.

16. The device of claim 14, wherein the optical members in combination are configured such that the device has an optical path difference less than a value of the optical invariant divided by 450 times a midrange wavelength in the spectral range.

17. A device comprising:
an elongated tube configured for insertion into a body; and
at least two optical members located in the tube, wherein the optical members in combination are configured such that the device has an optical invariant-to-clear aperture semidiameter ratio greater than about 0.05, an optical path difference less than a value of the optical invariant divided by at least 250 times a midrange wavelength in a spectral range from about 435.8 to about 656.3 nanometers, and substantially corrects for chromatic aberrations throughout a spectral range from about 435.8 nm to about 656.3 nm.

18. A method comprising:
conducting polychromatic light through at least two optical members of a device, the optical members being located in an elongated tube configured for insertion into a body, wherein the members in combination are configured such that the device has an optical invariant-to-clear aperture semidiameter ratio greater than about 0.05, an optical path difference less than a value of the optical invariant divided by at least 250 times a midrange wavelength in a spectral range from about 435.8 to about 656.3 nanometers, and substantially corrects for chromatic aberrations throughout a spectral range from about 435.8 nm to about 656.3 nm.

* * * * *

UNITED STATES PATENT AND TRADEMARK OFFICE
CERTIFICATE OF CORRECTION

PATENT NO. : 7,733,584 B2
APPLICATION NO. : 11/744810
DATED : June 8, 2010
INVENTOR(S) : Yuri Kazakevich It is certified that error appears in the above-identified patent and that said Letters Patent is hereby corrected as shown below:

In the Specification

Col. 3, line 33, after "nm or", insert --above--.

Col. 3, line 54, replace "M1-Mn" with --$M_1$-$M_n$--.

Col. 4, line 21, replace "55" with --550--.

Col. 5, line 33, replace "metric m" with --metric M--.

Col. 6, line 48, after "720", insert --TV--.

Col. 7, line 47, replace "plane" with --planes--.

Col. 7, line 63, replace "Table 2" with --Table 1--.

Col. 9, line 21, replace "97" with --98--.

Col. 10, line 2, replace "plan" with --plane--.

Col. 11, line 19, replace "a11, b11, c11" with --$a_{11}$, $b_{11}$, $c_{11}$--.

Col. 11, line 20, replace "a12, b12, c12" with --$a_{12}$, $b_{12}$, $c_{12}$--.

Col. 12, line 23, after "system", insert --with--.

Col. 12, line 33, replace "view" with --view. For example, the criteria are applied to about seventy percent of the field of view--.

Signed and Sealed this
Eleventh Day of February, 2014

Michelle K. Lee
*Deputy Director of the United States Patent and Trademark Office*

In the Claims

Claim 4, Col. 13, line 9, replace "second" with --second,--.

Claim 6, Col. 13, line 13, replace "side" with --sides--.

Claim 15, Col. 14, line 8, replace "device" with --method--.

Claim 16, Col. 14, line 13, replace "device" with --method--.